United States Patent
Ercolani et al.

(10) Patent No.: US 6,337,395 B1
(45) Date of Patent: Jan. 8, 2002

(54) MACROCYCLIC PORPHYRAZINE-TYPE COMPOUNDS, METAL DERIVATIVES THEREOF AND PROCESS FOR THEIR PREPARATION

(75) Inventors: Claudio Ercolani, Rome (IT); Pavel Stuzhin, Ivanovo (RU); Maria Pia Donzello, Rome (IT); Elvira Maria Bauer, Rome (IT); Demetria Cardarilli, Rome (IT); Rita Agostinetto, Frascati (IT)

(73) Assignee: Universita Degli Studi Di Roma "La Sapienza", Rome (IT)

( * ) Notice: Subject to any disclaimer, the term of this patent is extended or adjusted under 35 U.S.C. 154(b) by 0 days.

(21) Appl. No.: 09/509,217

(22) PCT Filed: Sep. 24, 1998

(86) PCT No.: PCT/IT98/00255

§ 371 Date: Sep. 20, 2000

§ 102(e) Date: Sep. 20, 2000

(87) PCT Pub. No.: WO99/15533

PCT Pub. Date: Apr. 1, 1999

(30) Foreign Application Priority Data

Sep. 24, 1997 (IT) ........................................ RM97A0577

(51) Int. Cl.[7] .................. C07D 285/14; C07D 293/12; C07D 417/14; C07D 421/14
(52) U.S. Cl. ........................................ 540/121
(58) Field of Search ........................................ 540/121

(56) References Cited

FOREIGN PATENT DOCUMENTS

| DE | 39 41 279 A | 6/1990 |
|---|---|---|
| DE | 0 418 611 | 3/1991 |

OTHER PUBLICATIONS

Stuzhin et al. Inorg. Chem. 37 (1998) 1533–1539.*
Morkved et al., "Template Assisted Cyclotetramerisations of 1,25–Thiadiazole–3,4–dicarbonitrile," Acta Chemica Scandinavica, 1994, 48;912–916.
Morkved et al., "Preparations and Template Cyclotetramerisations of 2,1,3–Benzothia(selena)diazole–5,6–dicarbonitriles," Acta Chemica Scandinavica, 1995, 49: 658–662.
Database WPI, Week 9043, Derwent Publications Ltd., London; GB; AN 90–324585 & JP 02 232267, Sep. 14, 1990.
Database WPI, Week 9043, Derwent Publications Ltd., London; GB; AN 90–324586 & JP 02 232268, Sep. 14, 1990.
Chemical Abstracts, vol. 125, No. 5, Jul. 29, 1996, abstract No. 58180.
Chemical Abstract, vol. 119, No. 20, Nov. 15, 1993, abstract No. 216163.
Chemical Abstracts, vol. 119, No. 2, Jul. 12, 1993, abstract No. 19270.
Christie et al., "Tetraieno[2,3–b]porphyrazines: Thiophene Analogues of Phthalocyanines: A Re–Investigation," Dyes and Pigments, 1997 vol. 333, No. 2, pp. 107–118.
Worhle et al., "A Simple Synthesis of 4,5–Disubstituted 1,2–Dicyanobenzenes and 2,3,9, 10, 16, 17, 23, 24–Octasubstituted Phthalocyanines," 1993, pp. 194–196.
Gurek et al., "Octakis(alkylthio)–substituted Phthalocyanines and their Interactions with Silver(1) and Palldium(II) Ions," J. Chem. Soc. Dalton Trans., 1994, pp. 1419.
Chemical Abstracts, vol. 119, No. 8, Aug. 23, 1993, abstract No. 74578.

* cited by examiner

Primary Examiner—John M. Ford
(74) Attorney, Agent, or Firm—Browdy and Neimark

(57) ABSTRACT

The invention relates to new macrocyclic phthalocyanine-like systems. In particular, object of the invention are new macrocyclic porphyrazine-type compounds and metal derivatives thereof, in which heterocycle rings are provided at the periphery of the inner porphyrazine fragment. A further object of the invention is a process for obtaining, as an example, tetra(thiadiazolo)porphyrazine, or tetra (selenediazolo)porphyrazine, by means of cyclotetramerization of the monomers 3,4-dicyano-1,25-thiadizole, or 3,4-dicyano-1,2,5-selenodiazole with metallorganico or inorganic salts, in organic solvents, extraction, if any, of the metal from the complexes thus formed by treatment with strong acids to obtain tetra(thiadiazolo)porphyrazine, or tetra(selenediazolo)porphyrazine, and by treatment, if any, of these compounds with a metallorganic or inorganic salt to obtain the metal derivatives thereof different from those previously extracted.

7 Claims, No Drawings

MACROCYCLIC PORPHYRAZINE-TYPE COMPOUNDS, METAL DERIVATIVES THEREOF AND PROCESS FOR THEIR PREPARATION

CROSS REFERENCE TO RELATED APPLICATION

The present application is the national stage under 35 U.S.C. 371 of PCT/IT98/0025, filed Sep. 24, 1998.

DESCRIPTION

1. Technical Field

The present invention relates to new macrocyclic systems of porphyrazine-type and their metal derivatives, characterized by the presence of heteroatoms at the periphery of the macrocyclic ring.

This new series of compounds of porphyrazine-type supplement the class of compounds so called "phthalocyanines" ("The Phthalocyanines", F. H. Moser, A. L. Thomas, Eds.; CRC Press, Boca Raton, Fla., Vol. 1 and II, 1983), comprising the phthalocyanine and the metal derivatives thereof, already known since the 1930s (R. P. Linstead and al., J. Chem. Soc., 1936, 1016, and later works), as laboratory synthetic products and having a molecular structure bringing to mind that of analogue synthetic and natural porphyrines ("The porphyrines", D. Dolphin, Ed.; Acad. Press Inc.; New York; Vols. I–VII (1979)).

2. Background Art

It is well known from the last 50 years literature that the phthalocyanines as such and as the derivatives thereof having various substituents on the peripheral benzene rings, have been the object of a large interest both in basic researches and for researches of applicative type ("Phthalocyanines: Properties and Applications", C. C. Leznoff, A.B.P. Lever, Eds., VCH Publ., New York, Vols. I–IV (1989–1996). They are intensively studied as special materials for forming thin films, for applications in the fields of sensors, electric conductivity and semiconductivity, electrochromics, liquid crystals, catalysis, non-linear optic properties, graphic reproduction, but also for practical interest aspects, such as the preparation of inks and dyes for textiles, to mention only some among those of present major interest. It ensues that the phthalocyanines are manufactured and put into the market by big chemical industries and by industries specialized in research purposes, among which Carlo Erba, Aldrich (U.S.A.) and Fluka (Germany).

Valid alternatives do not seem to have resulted from attempts made in the last years to supplement the pthalocyanines with new classes of compounds, similar in molecular and electronical structure, but having innovative elements such as to allow an equal broad utilization in the development of basic research and new specialistic applications.

DISCLOSURE OF THE INVENTION

The new phthalocyanine-like systems, according to the present invention, open the possibility of new scientific investigations, with potential capabilities of broader technological applications in fields of great importance both for the basic research and industrial field utilization.

Object of the present invention are macrocyclic porphyrazine-type compounds and the metal derivatives thereof, characterized by the fact of comprising rings of heterocycle type at the periphery of the inner porphyrazine fragment.

The new macrocyclic compounds according to the present invention have, at the periphery of the inner porphyrazine fragment, a ring of selenodiazole type, and they show the following structural formula (I)

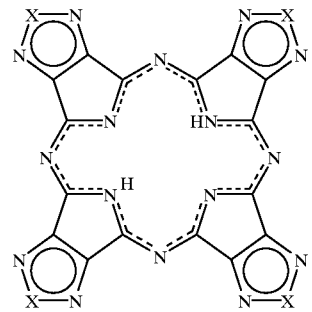

in which X is Se.

A further object of the present invention are the metal derivatives of the above mentioned molecules.

Hereinafter the molecule with the thiadiazole ring and the metal derivatives thereof will be also indicated as I-a, whereas the molecule according to the invention with selenodiazole ring and the metal derivatives thereof will be also indicated as I-b.

An additional object of the present invention is a process for the preparation of the macrocyclic compounds (1) and the metal derivatives thereof, characterized by cyclotetramerizating the monomers 3,4-dicyano-1,2,5-thiadiazole, or 3,4-dicyano-1,2,5-selenodiazole in an organic solvent by reaction with Mg(II) as a template, in the form of alcohoxylate, in the presence of a small amount of $I_2$ as a catalyst or by reaction with inorganic salts, eventual extraction of the metal by treatment with strong acids from the formed complexes to obtain tetrakis(thiadazole) porphyrazine, or tetrakis(selenodiazole)porphyrazine, and eventual treatment of these compounds by a metallorganic or inorganic salt to obtain the metal derivatives thereof different from the previously extracted metals.

DETAILED DESCRIPTION OF THE INVENTION

In the process according the present invention, the inorganic salt used for the cyclotetramerization can be a salt of a metal selected from the group comprising Mg(II), Al(III), Ga(III) and In(III). The extraction of the metal from the formed complexes can be obtained with strong acids selected from the group comprising acetic acid, trifluoroacetic acid and sulphuric acid.

In a particular embodiment of the present invention, the preparation of a specific compound of formula (1) and, from that, of a series of metal derivatives, is carried out starting from monomer species comprising 3,4-dicyano-1,2,5-thiadiazole (DCTD) and from the corresponding selenium monomer (DCSeD), obtained from commercially available (Carlo Erba, Aldrich, Fluka) diaminomaleodinitryl

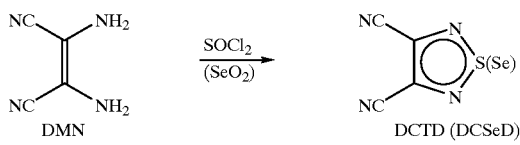

(DMN), and thionyl chloride respectively (yield 80–90%), following a process already described in the literature (G. Ribaldone, R. Grecu, Germ. Pat. 2651604 (1977), Chem. Abst., 87, 1977, 135344) and $SeO_2$. For DCSeD, the same reagents (DMN and $SeO_2$) have been used by Shew (D. Shew, Diss. Abstr., 20, 1959, 1593; Chem. Abstr. 54, 4548a). We have observed that by stirring DMN with $SeO_2$ in $CH_2Cl_2$, DCSeD was obtained with a practically theoretical yield (97–100%). Some authors instead prepared DCSeD from diiminosuccinonitryl and $SeO_2$, but with a lower yield (H. W. Roesky, T. Gries, H. Hofman, J. Schimkowiak, P. G. Jones, K. Meyer-Bäse, G. M. Sheldrik, Chem. Ber., 119, 1986, 366).

The process of cyclotetramerization of the monomers DCTD and DCSeD can be operated by reaction with Mg(II) as a template in alkoxylate form (such as propoxylate, butoxylate), in the presence of small amounts of $I_2$ as a catalyst. The metal can be extracted from the Mg(II) complex by treatment with strong acids ($CH_3COOOH$, $CF_3COOH$, $H_2SO_4$) to obtain the compound (1). The preparation of other metal derivatives can proceed from the compound (1) by selecting a new metal respectively in form of an organic or inorganic salt (such as acetate, chloride, sulphate and the like) and under suitable conditions of temperature and reaction means (dimethylsulphoxide, pyridine, quinoline, γ-picoline and the like). The reaction sequence, starting from DCTD, has the schema outlined as follows:

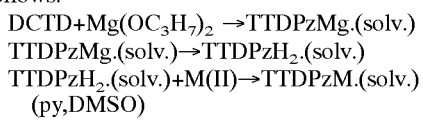

(py,DMSO)

A similar schema applies to the case of DCSeD.

The new macrocyclic compounds according to the invention show in common with the phtalocyanine class: a) the central porphyrazine fragment; b) the substantially square, planar structure of the whole macrocycle compound, in view of the peculiar structural characteristics of the thiadiazole and selenodiazole rings; c) wide delocalization of π electrons which, is similarly to phthalocyanines, extend throughout the molecular system. It is to be noted that, as in the thiadiazole and selenodiazole rings the number of π electrons is the same as that in the benzene ring, the new molecular systems provided in the present invention are isoelectronic to the phthalocyanines under this aspect.

The basic and interesting feature distinguishing the compounds described in the present invention from the phthalocyanine class resides in the presence of heteroatoms (N, S, Se) at the periphery of the macrocyclic ring. The spectroscopic behaviour in the visible UV region of the new systems shows that such presence produces differentiation features in the distribution of the π electron charge inside the molecular system of the macrocycles. In addition, the S and Se atoms, having "soft" atom characteristics, represent a strong novelty item. In fact they necessarily produce a peculiar situation of the contacts of one molecule to the other in the solid state. This has been shown to be of extreme importance in the field of the phthalocyanines as materials having, to say, electric conductivity properties, as such or after undergoing an oxidative doping. The additional advantageous property of the new class of macrocycle compounds is the general tendency thereof to attract molecules or metal ions at the periphery of the macrocycle ring essentially in view of the presence of the nitrogen atoms. For instance both of the macrocycle ligands of formula (I), and the respective metal derivatives are generally obtained in the air in the form of hydrates as a consequence of an engagement of $H_2O$ molecules at the macrocycle periphery. In addition this has influence on the solid state or of any other nature crystal, and on the possible interactions between the macrocycles in the solid state itself.

Herein before a general description of the invention has been presented. A more detailed description of specific embodiments will be given hereinafter with reference to the following examples, aiming at enhancing the objects, features and advantages of the invention. In particular the examples show some methods concerning the derivatives containing the thiadiazole ligand. Similar methods also apply to the corresponding products containing selenium.

EXAMPLE 1

Preparation of [TTDPzMg($H_2O$)].$CH_3COOH$

The hydrated Mg(II) Tetrakis(thiadiazole)porphyrazinate is prepared according to the following method.

Mg Grignard scrapings (750 mg; 30,8 mmols) activated with Hcl 1 N, n-propyl alcohol previously distilled on CaO or Na (30 ml), a few $I_2$ crystals having catalyst function, are introduced in a 100 ml two-necks flask. The flask is provided with a bubble cooler having a $CaCl_2$ pipe at its upper end and the reaction mixture is boiled for 19 hours. The DCTD (4,22 G; 30 mmols) is added to the reaction mixture and it is refluxed for additional 16 hours. After cooling and removing the propanol, the solid is washed with $CH_2Cl_2$ to remove the unreacted DCTD. Then the solid is suspended under stirring for one hour in 50% $CH_3COOH$ for separation of excess magnesium propylate. The suspension is filtered and the separated solid is washed with water to neutrality and dried under vacuum (1,95 g; yield about 45%). The so obtained complex corresponds to formula [TTDPzMg($H_2O$)].($CH_3COOH$). The content of $H_2O$ and $CH_3COOH$ slightly varies from sample to sample.

EXAMPLE 2

Preparation of the Macrocylic Ligand (I) Containing S [TTDPzH$_2$]

The solvated magnesium complex (1,95 g; about 3,42 mmols) is introduced into a 50 ml one-neck flask containing 10 ml $CF_3COOH$. The violet coloured suspension is boiled for 2 hours. 10 ml of water are cautiously added and it is refluxed for additional 20 minutes. After cooling the solid is separated by centrifugation, washed from the washings with water to neutrality and brought to constant weight under vacuum. A purple coloured powder (412 mg; yield 21,3%) is obtained, corresponding to TTDPzH$_2$ containing small amounts of carboxylic acid and $H_2O$, varying slightly from preparation to preparation. The solvated compound can be heat-sublimated under vacuum (400–450° C., 1,333 Pa [$10^{-2}$ mmHg]) to obtain TTDPzH$_2$.

EXAMPLE 3

Preparation of TTDPzCu

This complex can be prepared from the corresponding Mg(II) solvated complex and copper acetate (in excess) in trifluoroacetic acid by refluxing the mixture for 14 hours, successive addition of $H_2O$ (with caution) and further heating for 15–30 minutes, to which follows a heat treatment (300° C.) under vacuum (1,333 Pa [$10^{-2}$ mmHg]) for 1 hour of the solid so separated (yield 45–50%). The complex can also be obtained by a reaction at room temperature of solvated TTDPzH$_2$ and copper acetate (in excess) in pyridine, maintaining the mixture under stirring for 24 hours, and following separation, washing with ethanol and treatment under vacuum of the so obtained solid (yield 60%).

The Mg(II) and Cu(II) complexes of the class I-a have been illustrated in the prior art with preparation methods different from the ones herein before described. These methods, however, involve a difficult purification of the isolated materials, show elemental analysis data of unreliable interpretation and provide, at least in one case (Mg(II)), extremely low yields (E. H. Mørkved, S. M. Neset, H. Kjøsen, G. Hvistandahl, F. Mo, Acta Chem. Scand., 1994, 48, 912).

As to the macrocyclic ligand containing Se (TSeDPzH$_2$), and the Mg(II) and Cu(II) derivatives thereof, belonging to the class I-b, the synthesis methods are similar to those referenced as to the corresponding thiadiazole species, with variations only with respect to the additioned molecules ($H_2O$, carboxylic acid).

The preparation methods of the metal derivatives of the sulphur-containing macrocycle (TTDPzH$_2$) described herein below, apply to non-critical experimental conditions and most of the compounds so obtained are stable in air. The complexes can hold in some cases molecules of the solvent medium which are coordinated to the central metal (py, DMSO), and in all cases H$_2$O molecules weakly linked to the peripheral part of the molecule.

The so prepared complexes correspond to general formulas of the kind:

1) [TTDPzM(py)$_2$] (H$_2$O)$_x$(M=Mn(II), Fe(II), Co(II), Ni(II); x≅2)
2) [TTDPZM(DMSO)$_2$] (DMSO)$_x$(M=Mn(II), Fe(II); x=0–1)
3) [TTDPZM] (H$_2$O)$_x$(in general x≅2) (M=Mn(II), Fe(II), Co(II), Ni(II), Zn(II));
4) [TTDPZM] (M=Mn(II), Fe(II), Co(II), Ni(II), Zn(II)
5) [TTDPZM(X)] (H$_2$O)$_x$(M=Al(III), Ga(III), In(III); X=Cl, Br; x≅2)

Composition variations, as far as similar complexes derived from TSeDPzH$_2$ are concerned, are observed only in relation to the nature and the number of neutral molecules added (H$_2$O, carboxylic acid, DMSO, Py).

EXAMPLE 4

The compounds of class 1) are obtained using pyridine as a reaction medium, inert environment (Fe, Mn), boiling temperature of the solvent, reaction time of 1–3 hours, with yields higher than 80–85%. Aa an example the method is illustrated for the species [TTDPzFe(Py)$_2$] (H$_2$O )$_x$(X≅2).

In a 50 ml two-necks flask pyridine is degassed under N$_2$ current for 5 minutes and, under N$_2$ current, Mohr salt (300 mg; 0,75 mmols) and TTDPzH$_2$ (248 mg; about 0,45 mmols). are added. The mixture is refluxed in an N$_2$ atmosphere for 5 hours. After cooling, the solid product is separated by centrifugation, washed with water to remove the remaining Mohr salt in excess, and brought to constant weight under vacuum (300 mg; yield about 83%).

EXAMPLE 5

The compounds of class 2) are obtained using the DMSO as a reaction medium, inert environment, temperature of about 200° C., reaction time of 3 hours, with yields higher than 80–85%. The synthesis method is reported with reference to the complex TTDPzFe(DMSO)$_2$:

In a 50 ml two-necks flask are introduced, under N$_2$ current, freshly distilled DMSO (20 ml), Mohr salt (348 mg; 0.89 mmols) and solvated TTDPzH$_2$ (271,8 mg; about 0,50 mmols). The mixture is brought to a temperature of 200° C. and it is maintained under stirring for 3 hours in inert environment. After cooling the reaction mixture is centrifugated, and the dark green solid is washed several times with H$_2$O to remove the Mohr salt in excess and it is brought to constant weight under vacuum (320 mg; yield about 85%).

EXAMPLE 6

Interconversion of the species belonging to the classes 1) and 2). As an example reference is made to the Fe(II) case: [TTDPzFe(py)$_2$](H$_2$O)$_2$ and [TTDPzFe(DMSO)$_2$].

Complex [TTDPzFe(py)$_2$] (H$_2$O)$_2$ can be transformed into an analogue thereof containing DMSO by refluxing the starting complex in anhydrous and freshly distilled DMSO for 2–3 hours. The inverse reaction (DMSO→py, H$_2$O) is brought about by heat-boiling a complex suspension containing DMSO in pyridine for about 2 hours.

EXAMPLE 7

The compounds of class 3), with the exclusion of those containing Fe(II) and Mn(II), are obtained directly from TTDPzH$_2$ and an excess of the metal salt, by refluxing the reaction mixture for 2–3 hours in DMSO (or even in pyridine in the case of Cu(II) and Zn(II)). The Fe(II) and Mn(II) complexes are obtained from the corresponding complexes of classes 1) and 2) by heat treatment (300° C.) under vacuum (10$^{-2}$ mmHg) for 1–2 hours, followed by exposition to air of the products obtained, or by dissolving into acids (for instance 96% H$_2$SO$_4$) and reprecipitation in iced H$_2$O. This method is reported as an example in the case of Zn(II):

In a 25 ml Erlenmeyer flask containing pyridine (10 ml) TTDPzH$_2$ (224 mg; about 0,41 mmols) and hydrated zinc acetate (235 mg; 1.07 mmols) are introduced. The blue suspension is stirred at room temperature for 3 hours. The solid is separated by centrifugation, washed with water and ethanol and eventually brought to constant weight under vacuum. A purple powder (233 mg; yield about 87%) is obtained. Both IR spectrum and thermogravimetric analysis suggest the formation of an hydrated product, TTDPzZn (H$_2$O)$_x$(x=2–4).

EXAMPLE 8

The complexes of class 4 are obtained by full desolvation of the species belonging to classes 1), 2) and 3), such desolvation being obtained by heat treatment under vacuum (classes 1) and 2)): 10$^{-2}$ mmHg, 300° C., 1 hour; class 3): 10$^{-2}$ mmHg, 100° C., 1 hour, or by sublimation under vacuum (10$^{-2}$ mmHg) at a high temperature (400–500° C.).

EXAMPLE 9

The products of class 5) are obtained by a direct cyclotetramerization method from DCTD and anhydrous metal halogenide in a dry environment using a boiling heterocycle base (for example quinoline) as a reaction means.

ABBREVIATIONS

DMN, diaminomaleodinitryl
DCTD, 3,4-dicyano-1,2,5-thiadiazole
DCSeD, 3,4-dicyano-1,2,5-selenodiazole
DMSO, dimethylsulphoxide
Py, pyridine
TSeDPzH$_2$, tetrakis(selenodiazole)porphyrazine
TTDPzH$_2$, tetrakis(thiadiazole)porphyrazine

What is claimed is:

1. A macrocyclic compound of prophyrazine-type or a metal derivative thereof, comprising rings of heterocycle-type at the periphery of a porphyrazine inner fragment, said rings being selenodiazole, showing the following structural formula (I):

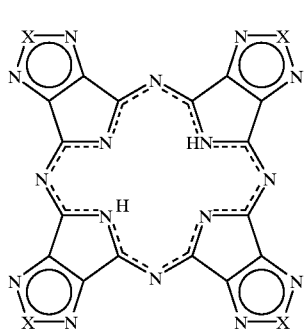

(I)

where X is Se.

2. A process for the preparation of a macrocyclic compound of porphyrazine-type or a metal derivative thereof showing the following structural formula (I):

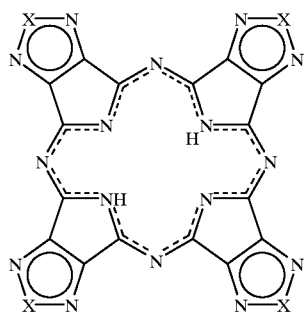

(I)

wherein X is selected from the group consisting of S and Se, said process comprising:

a step wherein a monomer 3,4-dicyano-1,2,5,-thiadiazole, or 3,4-dicyano-1,2,5,-selenodiazole, is cyclotetramerized in an organic solvent by reaction with Mg(II) as a template, in the form of alkoxide, in the presence of a small amount of $I_2$ as a catalyst or by reaction with an inorganic salt;

extraction of the metal derivative from the metal complex formed in the previous step by treatment with a strong acid, to obtain tetrakis(thiadiazole)porphyrazine or tetrakis(selenodiazole)porphyrazine; and optional treatment of said compound with a metallorganic or inorganic salt to obtain a metal derivative different from that obtained in the first step.

3. A process for the preparation of a macrocyclic compound or a metal derivative thereof according to claim 2, wherein the inorganic salt used for the cyclotetramerization is a salt of a metal selected from the group consisting of Mg(II), Al (III), Ga(III) and In(III).

4. A process for the preparation of a macrocyclic compound of porphyrazine-type or a metal derivative thereof according to claim 2, wherein the extraction of the metal from the so formed complex is obtained with a strong acid selected from the group consisting of acetic acid, trifluoroacetic acid and sulfuric acid.

5. A process according to claim 2, wherein the alkoxide is selected from the group consisting of propoxide and butoxide.

6. A process according to claim 3, wherein the alkoxide is selected from the group consisting of propoxide and butoxide.

7. A process according to claim 4, wherein the alkoxide is selected from the group consisting of propoxide and butoxide.

* * * * *